United States Patent [19]

Philpot

[11] Patent Number: 4,567,137

[45] Date of Patent: * Jan. 28, 1986

[54] SERUM THROMBIN TIME IN CLINICAL MEDICINE

[76] Inventor: Van B. Philpot, P.O. Box 312, East Houston, Miss. 38851

[*] Notice: The portion of the term of this patent subsequent to Jan. 20, 2000 has been disclaimed.

[21] Appl. No.: 609,817

[22] Filed: May 14, 1984

Related U.S. Application Data

[63] Continuation-in-part of Ser. No. 459,494, Jan. 20, 1983, Pat. No. 4,461,830.

[51] Int. Cl.⁴ .................... G01N 33/48; G01N 33/68; G01N 33/86; G01N 33/96

[52] U.S. Cl. .......................................... 435/13; 73/55; 128/637; 436/69

[58] Field of Search .............. 435/13; 73/55; 128/637; 436/69

[56] References Cited

U.S. PATENT DOCUMENTS

| | | | |
|---|---|---|---|
| 3,342,063 | 9/1967 | Smythe | 73/55 |
| 3,861,197 | 1/1975 | Adler | 436/69 X |
| 3,911,728 | 10/1975 | Fixot | 73/55 |
| 3,960,669 | 6/1976 | Innerfield | 435/13 |
| 3,990,947 | 11/1976 | Butler | 435/13 |
| 3,999,538 | 12/1976 | Philpot | 128/637 |
| 4,081,242 | 3/1978 | Girolami | 422/73 X |
| 4,083,363 | 4/1978 | Philpot | 128/637 |
| 4,165,632 | 8/1979 | Weber | 73/55 |
| 4,300,551 | 11/1981 | Kinney | 128/637 X |
| 4,461,830 | 7/1984 | Philpot | 435/13 |

OTHER PUBLICATIONS

Chemical Abstracts, 91:72753z (1979).
Chemical Abstracts, 95:59360y (1981).

*Primary Examiner*—Sidney Marantz
*Attorney, Agent, or Firm*—Cushman, Darby & Cushman

[57] ABSTRACT

A solution of purified, standardized fibrinogen is added to a sample of coagulant-free serum from subject, and the serum thrombin time is determined. The measurement may be related to diagnosing an abnormal body condition, such as schizophrenia, or selecting the optimum chemotherapeutic agent in treatment.

6 Claims, No Drawings

SERUM THROMBIN TIME IN CLINICAL MEDICINE

CROSS REFERENCE TO RELATED APPLICATIONS

This application is a continuation-in-part of my earlier application Ser. No. 459,494 filed Jan. 20, 1983, now U.S. Pat. No. 4,461,830.

BACKGROUND OF THE INVENTION

The measurement of the flow of blood through a device to measure blood viscosity, termed rheocohesion in the art, is a valuable diagnostic procedure. However, problems in obtaining a correct rheocohesion value include: improper venipuncture causing artifacts in the readings so obtained; special equipment is needed to accurately measure the rate of flow of blood through a hypodermic needle inserted directly into the blood vessel of a patient under study while maintaining controlled conditions of standard pressure, temperature and time; whole blood rheocohesion is an indirect measurement, and artifacts such as the hematocrit and total serum protein must be considered.

Direct measurement of whole blood rheocohesion is described in my earlier U.S. Pat. No. 3,999,538 and the apparatus described in my U.S. Pat. No. 4,083,363.

It would be convenient to obtain a single blood sample for numerous blood testing purposes from the patient using conventional syringe and/or vacutainer without specialized equipment of the type referred to above.

I have now found, and hereby disclose, a procedure for measuring the time required for the serum of a patient to coagulate a standardized solution of fibrinogen or serum thrombin time, and of correlating the times so obtained with whole blood rheocohesion. Serum thrombin time values are useful in diagnosis of numerous abnormal conditions, for instance myocardial infarction, stroke, transient ischemic attack, hysterical conversion syndrome, and schizophrenia.

Another significant application for serum thrombin time is in the monitoring of drug treatment for these condition.

Plasma is the clear liquid when whole blood is placed in an anticoagulant and the cellular elements of the blood settle to the bottom. Plasma is routinely obtained in blood banks by physical separation, i.e., centrifuge, to separate the cellular elements by gravity, from the clear, straw-colored liquid. The serum obtained for use in the present invention is withdrawing a blood sample from the patient and placed in a container without an anticoagulant, allowing the blood to clot then centrifuging to separate the cellular elements from the clear liquid. Serum thus obtained is free from anti-coagulants. Without an anticoagulant the blood fibrinogen is converted into fibrin, a three-dimensional gelatin-like network of fibers. As such the fibrin network is separated by the centrifuge, or spun down, with the red cells leaving the clear liquid at the top; the serum thus treated, contains no fibrinogen. Serum, then, is the same as plasma minus fibrinogen.

It is important that no anticoagulant be used in the procedure. The object of this procedure is to omit the patient's fibrinogen and to use the serum to analyze factors that influence purified, standardized fibrinogen, as discussed in more detail below.

In conventional rheology, the term "whole blood viscosity" refers primarily to values obtained by placing anticoagulated blood in rotational viscometers at varying shear rates. Since the results reported in my application are quite different from those of conventional viscometers and since entirely different phenomena are measured, the term rheocohesion is used below in place of viscosity.

Determination of Whole Blood Rheocohesion

The rheocohesive meter preferred for use in the present invention consists of a 10.0 ml syringe attached by a three-way stop cock and connecting tubing to a compound pressure gauge as shown, for example, in my earlier U.S. Pat. Nos. 3,999,538 and 4,083,363, disclosures of which are hereby incorporated by reference. In the preferred embodiment the gauge is protected from contamination by blood is a Gelman filter Acrodisc C R. A ¾ in. 21 gauge needle attached to a 6-inch butterfly tubing is used for the venipuncture.

A blood pressure cuff is placed around the forearm and inflated to 30 mm Hg. Using sterile precautions a venipuncture is performed in the antecubital vein and blood is allowed to flow into the system giving a reading on the positive pressure side of the gauge. When the flow of blood becomes stabilized, this reading is recorded as the venous pressure. Blood is then withdrawn into the syringe at a standard negative pressure for a specified period of time (usually 80 mm mercury for 15 seconds). The negative pressure is then added to the venous pressure to give the combined hydrostatic pressure forcing blood into the syringe.

The entire instrument, including the butterfly needle and syringe, is calibrated using distilled water at 37° C. as a standard. A graph is constructed showing the amount of distilled water withdrawn into the syringe at varying negative pressures for the standard period of time used in this procedure. From the graph one determines the amount of distilled water that can be drawn into the system using the total hydrostatic pressure of withdrawing blood in a test situation. The volume of blood withdrawn under a test situation is then divided into the volume of distilled water withdrawn and the result is expressed in total rheocohesive units (TRU).

The total rheocohesiveness of blood is determined to a large extent by the hematocrit and it was considered advisable in psychiatric patients to exclude the hematocrit as a variable. Four hundred fifty ml of blood was withdrawn from a normal volunteer in a blood bank and placed in a plastic bag containing 63 ml of CPDA-1 soln. as an anticoagulant. The plasma was separated from the cells and reconstituted at levels of 10%, 20%, 30%, 40%, 50%, 60%, and 70% hematocrits. Rheocohesion values were determined and a relationship determined when rheocohesive units are plotted against hematocrit. Between the values of 30 to 60% hematocrit the curve is relatively straight and the rheocohesiveness of blood increases 0.043 units for each 1.0% hematocrit. Using this factor corrections can be made to a level of 40% hematocrit thus eliminating the hematocrit as a variable in the final result. These results are reported as corrected rheocohesive units (CRU). The TRU of males is greater than females while there is no significant difference in the CRU of males and females.

Other instruments for measuring serum and plasma viscometers may be used.

As described in detail in my previous application Ser. No. 459,494, rheocohesion of blood of schizophrenic patients is above normal; this finding is associated with an abnormal reaction of schizophrenic serum with purified fibrinogen. Neuroleptic drugs reduced the rheocohesion of schizophrenic patients and presumably also affected the thrombin level of schizophrenic serum. Accordingly, studies were undertaken to define the effects of normal serum on purified fibrinogen. Since aspirin is known to have an effect on prostaglandin synthesis and circulation of blood, the effects of aspirin on the reaction of normal serum and purified fibrinogen were studied. Mielke ("Standardized Bleeding Time and Its Prolongation by Aspirin", Blood 34:204, 1969) has shown that aspirin will prolong bleeding time. It seemed desirable therefore to correlate these findings with the bleeding time.

Measuring Serum Thrombin Time

A simple test for measuring serum thrombin time (STT) is as follows: A solution of human fibrinogen fraction I type III (Sigma) was prepared in normal saline at a concentration of 20.0 mg/dl. Samples of blood were withdrawn from the antecubital vein of normal young (18–40 yrs.) adults and allowed to stand at room temperature for 20 minutes until a clot was formed. The time of removal of blood was recorded. The samples were centrifuged at 3,000 rpm for 5 minutes and serum removed. Two-tenths ml of serum were added to 0.2 ml of fibrinogen solution and incubated at room temperature (25° C.). The tubes were tilted at intervals with the time running and observed for coagulation. The time required for coagulation was recorded and is referred to herein as serum thrombin time. The length of time from the withdrawal of blood sample until the performance of the serum thrombin time was also recorded. The time required for coagulation, or STT, is related to whole blood rheocohesion. Normal serum under these circumstances will give no increase in the serum thrombin time. The serum of schizophrenic patients, however, is biologically abnormal and will give an increase in the serum thrombin time.

Thrombin is an enzyme resulting from activation of prothrombin which catalyzes the conversion of fibrinogen to fibrin and I will thus refer to an enzyme in serum which clots fibrinogen as thrombin. Since thrombin is essential to the coagulation of blood before serum is obtained, other appropriate names might be "thrombin consumption test" or "thrombin residual test".

A relatively high concentration of fibrinogen (20.0 mg/dl) was used for maximal reproducibility of results. I have found that a weaker solution of fibrinogen, i.e., 1–3 mg/dl, will yield different results in the same serum sample whereas the more concentrated fibrinogen solution yields identical results on the same sample. Room temperature (25° C.) was used because the reaction is faster at this temperature than at the body temperature (37° C.). Alternatively, a more dilute fibrinogen solution may be used, for instance 3 mg/ml, however a smaller sample of serum is employed, a typical ratio being 1 part serum to 10 parts of fibrinogen solution. A temperature of 37° C. is used when employing the dilute solution.

While prolongation of bleeding time by aspirin has been reported in male volunteers, the females in the present study did not react as consistently as males in the response of bleeding time to aspirin. Furthermore, the relationship of response to bleeding time correlated poorly with serum thrombin time.

The specific procedure used in the following clinical studies was as follows: A solution of human fibrinogen fraction I type III (Sigma) was prepared in normal saline at a concentration of 20.0 mg/dl. Samples of blood were withdrawn from the antecubital vein of normal young (18–40 yrs.) adults and allowed to stand at room temperature for 20 minutes until a clot was formed. The time of removal of blood was recorded. The samples were centrifuged at 3,000 rpm for 5 minutes and serum removed. Two-tenths ml of serum were added to 0.2 ml of fibrinogen solution and incubated at room temperature (25° C.). The tubes were tilted at intervals with the time running and observed for coagulation. The time required for coagulation was recorded and is referred to herein as serum thrombin time. The length of time from the withdrawal of blood sample until the performance of the serum thrombin time was also recorded.

In one series of tests, 3 aspirin tablets (975 mg) were taken by volunteers in the fasting state and blood samples drawn 2 hours later. In a second series, 10 aspirin tablets were administered in 5 equally divided doses (2 aspirins every 5 hours over a period of 24 hours prior to drawing blood. In both series, a baseline of normal values was obtained, prior to the administration of aspirin.

For in vitro studies, a solution of aspirin was prepared at a concentration of 1 mg/dl in saline with pH adjusted to 8.8. A blood sample was removed from one volunteer and divided into two portions of 5.0 ml each. To one blood sample 0.2 ml aspirin solution was added and to the other 0.2 ml buffered saline was added. Serum thrombin times were performed simultaneously on the two samples 40 minutes and 60 minutes following removal of blood.

Bleeding time was performed by the method of Mielke (supra). Percent variation was calculated by subtracting results of these tests before and after aspirin and dividing this figure into the higher of the two values. A positive (+) % variation signifies prolongation of bleeding time or serum thrombin time by aspirin, whereas a negative (−) % variation signifies a decrease in bleeding time following aspirin.

Serum thrombin deteriorates rapidly following the withdrawal of blood from the vein. For this reason, the procedure was standardized for performance of serum thrombin time, 1 hour following the venipuncture. The bleeding time was performed immediately, before or after the venipuncture.

As shown in Table 1, aspirin consistently caused an increase in serum thrombin time in the normal male volunteers (total 8). Not included in this table are results of one male volunteer in a state of moderately servere malnutrition who showed a decrease in serum thrombin time. All 8 of the normal male volunteers showed a concomitant increase in bleeding time. There appeared to be no significant difference between the 2 hour 3 aspirin test and the 24 hour 10 aspirin test. The average change in serum thrombin time by aspirin was +45%.

Results with female volunteers showed that aspirin caused an increase in serum thrombin time in only 7 of 14 volunteers (50%). In 4 females aspirin actually caused a decrease in serum thrombin time and in 3 there was not significant difference. There appears to be some relationship to the menstrual cycle since one volunteer showed a decrease (−55%) in serum thrombin time following aspirin on the 2nd day of her menstrual period and an increase (+33%) on the 10th day of the menstrual cycle. The overall average of change in serum thrombin caused by aspirin in women was +10% in contrast to the +45% average in men. As was the case with men, there appeared to be no significant variation in the 2 hour 3 aspirin test and the 24 hour 10 aspirin test.

Bleeding time in females was prolonged by aspirin in 2 of 12 female volunteers and it can be seen from the raw data in Table 1 the correlation between bleeding time and serum thrombin time is erratic and inconsistent in the female. In vitro studies showed identical results in serum thrombin using aspirin and saline control. Tests were performed 40 minutes and 60 minutes following withdrawal of blood.

It should be understood that coagulation is a change in viscosity of fluid from the liquid state to the solid state. This type of viscosity change can be observed by the naked eye and does not require the use of an instrument as previously described.

TABLE 1

EFFECT OF ASPIRIN ON SERUM THROMBIN TIME (STT)* AND BLEEDING TIME (BT)

| | STT (seconds) | | BT (minutes) | | % change | |
|---|---|---|---|---|---|---|
| | Before Aspirin | After Aspirin | Before Aspirin | After Aspirin | STT | BT |
| 2 Hour 3 Aspirin Test | | | | | | |
| Male | 242 | 300 | 6.5 | 10.5 | +20 | +38 |
| | 175 | 360 | 4.0 | 6.0 | +52 | +33 |
| | 300 | 604 | 5.0 | 6.5 | +50 | +23 |
| | 247 | 3-2 | 6.5 | 9 | +18 | +27 |
| Female | 170 | 226 | not done | | +18 | +27 |
| | 197 | 219 | not done | | +25 | |
| | 206 | 151 | 6.0 | 10.5 | −27 | +43 |
| | 208 | 200 | 6.0 | 6.5 | −4 | +7 |
| | 314 | 470 | 8.0 | 7.0 | +33 | −15 |
| | 254 | 275 | 9.0 | 12.0 | +7 | +25 |
| | 670 | 300 | 8.5 | 8.0 | −55 | −5 |
| 24 Hour 10 Aspirin Test | | | | | | |
| Male | 256 | 3-2 | 4.5 | 6.5 | +15 | +31 |
| | 105 | 451 | 7.5 | 10.5 | +77 | +28 |
| | 90 | 330 | 6.5 | 8.0 | +73 | +31 |
| | 120 | 246 | 6.5 | 23 | +51 | +71 |
| Female | 398 | 353 | 6.0 | 6.0 | −12 | 0 |
| | 254 | 257 | 4.5 | 6.5 | +1 | +30 |
| | 209 | 204 | 12.5 | 19 | 0 | +34 |
| | 150 | 254 | 16.0 | 22.5 | +41 | +28 |
| | 359 | 280 | 6.5 | 10.5 | −28 | +42 |
| | 328 | 750 | 5.5 | 7.5 | +56 | +33 |
| | 246 | 292 | 6.0 | 8.0 | +16 | +24 |

*STT performed 1 hour after venipuncture.

The procedures described above allow the clinician an opportunity to monitor and observe the circulatory system consequences of a wide variety of chemotherapeutic agents. The U.S. Food and Drug Aministration reported in an FDA bulletin in February of 1980 that aspirin is effective in reducing the risk of recurrent ischemic attacks in males, but that there was no evidence of a similar effect in females. The sex difference in the response of serum thrombin to aspirin appears to correlate well with the prevention of thromboembolic disorders by aspirin.

What is claimed is:

1. A method of diagnosing an abnormal body condition of a subject animal comprising the successive steps of:
   (1) withdrawing a blood sample from the patient under study;
   (2) allowing the sample obtained to form a clot;
   (3) obtaining a sample of serum from the clot of step (2);
   (4) adding a solution of purified, standardized fibrinogen to a sample of the serum of step (3) and allowing the resulting mixture to incubate and coagulate;
   (5) measuring the time between the addition of the fibrinogen solution and coagulation to determine the serum thrombin time;
   (6) comparing the serum thrombin time measured in step (5) with a serum thrombin time of a normal population of patients when treated under conditions similar to those of steps (1)–(5); and
   (7) diagnosing an abnormal body condition of said subject in accordance with the values compared in step (6).

2. A method of selecting the optimum chemothereapeutic agent in the treatment of an abnormal body condition in a subject animal comprising the successive steps of:
   (1) withdrawing a blood sample from the animal under study;
   (2) allowing the sample obtained to form a clot;
   (3) obtaining a sample of serum from the clot of step (2);
   (4) adding a solution of purified, standardized fibrinogen to each of the serum samples allowing each of the resulting mixtures to incubate and coagulate;
   (5) measuring the time between the addition of the fibrinogen solution and coagulation to determine the serum thrombin time for the serum;
   (6) mixing a portion of the serum of step (3), or whole blood of step (1), with a solution of a candidate chemotherapeutic agent in a concentration approximating at least the minimum effective therapeutic concentration in the blood of a subject receiving the candidate chemotherapeutic agent at a predetermined dosage level or giving appropriate doses of drug to test animal;
   (7) repeating steps (1)–(5) after a predetermined time has lapsed following the administration of test drug to subject animal, blood, or serum;
   (8) comparing the serum thrombin time prior to administration of drug to test animal, blood, or serum with serum thrombin time after administration of drug;
   (9) comparing each of the serum thrombin times measured in step (8) with a predetermined averaged serum thrombin time of a normal population of patients when treated under conditions similar to those of steps (7) and (8); and
   (10) determining the candidate chemotherapeutic agent that effectively reduces the patient's serum thrombin time to approximate the predetermined serum thrombin time of the normal poplulation as compared in step (9).

3. The method of claim 2 wherein the incubation of steps (4) and (5) is at a temperature of about 20°–40° C.

4. The method of claim 2 wherein the ratio of serum to fibrinogen solution in step (4) is within the range of 1:1 to 1:20.

5. The method of claim 2 wherein the concentration of purified and standardized fibrinogen in the solution of step (4) is from 1 to 20 mg/ml.

6. The method of claim 5 wherein the concentration of fibrinogen is about 2 to about 3 mg/ml.